United States Patent
Prasitchoke et al.

(10) Patent No.: US 9,828,490 B2
(45) Date of Patent: Nov. 28, 2017

(54) BIO-BASED POLYMER ADDITIVE, A PROCESS FOR PREPARING THE BIO-BASED POLYMER ADDITIVE AND A BIODEGRADABLE POLYMER COMPOSITION COMPRISING SAID BIO-BASED POLYMER ADDITIVE

(71) Applicant: PTT GLOBAL CHEMICAL PUBLIC COMPANY LIMITED, Bangkok (TH)

(72) Inventors: Phatthanon Prasitchoke, Bangkok (TH); Nilubon Jong-Anurakkun, Bangkok (TH); Wasana Jamsak, Bangkok (TH); Chaya Chandavasu, Bangkok (TH); Montree Pleekhunt, Bangkok (TH)

(73) Assignee: PTT GLOBAL CHEMICAL PUBLIC COMPANY LIMITED, Bangkok (TH)

( * ) Notice: Subject to any disclaimer, the term of this patent is extended or adjusted under 35 U.S.C. 154(b) by 0 days.

(21) Appl. No.: 14/423,658

(22) PCT Filed: Aug. 30, 2013

(86) PCT No.: PCT/TH2013/000042
§ 371 (c)(1),
(2) Date: Feb. 24, 2015

(87) PCT Pub. No.: WO2014/035351
PCT Pub. Date: Mar. 6, 2014

(65) Prior Publication Data
US 2015/0225539 A1  Aug. 13, 2015

Related U.S. Application Data

(63) Continuation-in-part of application No. PCT/TH2013/000018, filed on Apr. 24, 2013.

(60) Provisional application No. 61/694,872, filed on Aug. 30, 2012.

(51) Int. Cl.
| | | |
|---|---|---|
| A23L 1/27 | (2006.01) |
| C09B 61/00 | (2006.01) |
| C12C 5/04 | (2006.01) |
| C08K 5/1545 | (2006.01) |
| C08L 67/00 | (2006.01) |
| C08L 89/00 | (2006.01) |
| C08L 99/00 | (2006.01) |
| C08L 101/16 | (2006.01) |
| C07C 7/00 | (2006.01) |
| C07C 13/28 | (2006.01) |
| C07D 311/04 | (2006.01) |
| C07D 471/22 | (2006.01) |
| C08K 5/01 | (2006.01) |
| C08K 5/053 | (2006.01) |
| C08K 5/3415 | (2006.01) |
| C08K 5/3417 | (2006.01) |

(52) U.S. Cl.
CPC .............. $C08K\ 5/1545$ (2013.01); $C07C\ 7/00$ (2013.01); $C07C\ 13/28$ (2013.01); $C07D\ 311/04$ (2013.01); $C07D\ 471/22$ (2013.01); $C08K\ 5/01$ (2013.01); $C08K\ 5/053$ (2013.01); $C08K\ 5/3415$ (2013.01); $C08K\ 5/3417$ (2013.01); $C08L\ 67/00$ (2013.01); $C08L\ 89/00$ (2013.01); $C08L\ 99/00$ (2013.01); $C08L\ 101/16$ (2013.01)

(58) Field of Classification Search
None
See application file for complete search history.

(56) References Cited

U.S. PATENT DOCUMENTS

| | | |
|---|---|---|
| 3,336,141 A | 8/1967 | Frisina |
| 4,320,050 A | 3/1982 | Rebeller et al. |
| 4,574,086 A | 3/1986 | Shackelford |
| 5,545,557 A | 8/1996 | Hobson et al. |
| 5,686,296 A | 11/1997 | Hobson et al. |
| 6,338,861 B1 * | 1/2002 | Gozu ................... A23L 27/24 424/725 |
| 2003/0004479 A1 | 1/2003 | Ueda et al. |
| 2012/0101198 A1 * | 4/2012 | Cernohous ........... C08K 5/0033 524/101 |
| 2013/0018124 A1 | 1/2013 | Catinari |

FOREIGN PATENT DOCUMENTS

| | | |
|---|---|---|
| KR | 20110067477 A | 6/2011 |
| KR | 20120010468 A | 2/2012 |
| WO | 94/17132 A1 | 8/1994 |

OTHER PUBLICATIONS

International Search Report and Written Opinion for PCT International Application No. PCT/TH2013/000042 (dated Dec. 2, 2013).
International Search Report for PCT International Application No. PCT/TH2013/000018 (dated Nov. 4, 2013).

* cited by examiner

*Primary Examiner* — Robert T Butcher
(74) *Attorney, Agent, or Firm* — LeClairRyan, a Professional Corporation

(57) ABSTRACT

The present invention disclosed a bio-based polymer additive, its preparation process and a biodegradable polymer composition comprising the said bio-based polymer additive for use in manufacturing of biodegradable plastic. The said additive is prepared from the biomass of broken microorganism cell such as microalgae, yeast or other microorganisms. In particular, the bio-based polymer additive is for enhancing rheological properties and/or biodegradability of a polymer. In particular, the additive is for use as a pigment.

30 Claims, 9 Drawing Sheets
(9 of 9 Drawing Sheet(s) Filed in Color)

PBS + 1.0% algae pigment powder

PBS + 5.0% algae pigment powder

PLA + 1.0% algae pigment powder

PLA + 5.0% algae pigment powder

PBS + 1.0% yeast pigment powder

PBS + 5.0% yeast pigment powder

PLA + 1.0% yeast pigment powder

PLA + 5.0% yeast pigment powder

BIO-BASED POLYMER ADDITIVE, A PROCESS FOR PREPARING THE BIO-BASED POLYMER ADDITIVE AND A BIODEGRADABLE POLYMER COMPOSITION COMPRISING SAID BIO-BASED POLYMER ADDITIVE

This application is a national stage application under 35 U.S.C. 371 from PCT/TH2013/000042, filed Aug. 30, 2013, which is a continuation-in-part of PCT International Application No. PCT/TH2013/000018, filed 24 Apr. 2013 (designating the United States), and which claims the benefit of U.S. Provisional Patent Application Ser. No. 61/694,872, filed Aug. 30, 2012.

TECHNICAL FIELD OF THE INVENTION

The present invention relates to a bio-based polymer additive, a process for preparing the bio-based polymer additive and a biodegradable polymer composition comprising said bio-based polymer additive. According to a particular aspect, the bio-based polymer additive is for use as a pigment.

BACKGROUND OF THE INVENTION

The fast growing biotechnological industry is generating a new kind of pollution problem from solid residue from microorganism biomass. The microorganisms have been using as single cell factory, such as brewer yeast to produce ethanol via fermentation process where ethanol is used as alternative energy in the automotive industry wherein after purification of ethanol, yeast remains as by-product or waste.

Similarly, microalgae which are conventionally used in food production and food additive industries have in recent years come into the spotlight of the biofuel industry since several species are capable of producing oils and lipids. Microalgae are excellent candidates for fuel production because of their combined advantages of high-photosynthetic efficiency, biomass production and faster growth, as compared to other energy crops. Microalgae are grown in large-scale photobioreactors for the industrial-scale production of biofuel, consequently a huge amount of microalgae biomass remains after oil extraction process. After completion of the production processes, the discarded microorganisms remain as large amount of solid waste resulting in a new kind of pollution problem as aforementioned. To solve this pollution problem, there is a need to find a better way for disposal or add economic values of these microorganism wastes.

One of the common practices for disposal of the microbial solid waste by the biotechnology industry is to dispose tons of such waste as a landfill. Other several solutions have also been proposed. For instance, Shiho et. al., (2011) suggested that the waste of microalgae *Botryococcus* biomass can be used as heat generator in which the combustion heat of the solid component was observed experimentally and was found to be 31-34 MJ/kg with 3% moisture content. However, drying process before gaining that very low moisture content might be costly and inefficient. In another example, the yeast solid waste from bio-ethanol industry has been utilized as feed supplements. However, its consumption is very limited due to difficulties in quality control of yeast solid waste. Hence, the proposed application cannot be a sustainable solution to eliminate large amount of yeast biomass.

Another proposed solution to this problem is incorporating the biomass with plastics. U.S. Pat. No. 5,346,929 disclosed a method of preparation of resin made from mixture of synthetic biodegradable polymer and starch from fungi *Aspergillus* but the method/process of resin production including its advantage was unclear. U.S. Pat. No. 8,026,301 teaches the polymer composition comprising a complex of petroleum-based resin such as polyethylene, polypropylene, polystyrene, and polyvinyl chloride and cellulose, chemical based-nitrogen source, natural nutrient from blue-green algae or yeast in order to increase their biodegradability.

However, the incorporation of the biomass with plastics requires further supplementation of the additives, such as compatibility agents to maintain the polymer properties and their compatibilities otherwise the amount of biomass added in plastics would be very limited. Moreover, none of known methods teach or suggest a worthwhile technique to enhance the use of biomass not only to improve the biodegradability of biodegradable polymers but also to enhance properties, such as viscosity or compatibility, of biodegradable polymer compositions which are very vital in the production of biodegradable plastics.

Biodegradable plastics claim to be environmentally friendly. They can be produced from plants and its derivatives or other several renewable sources. Biodegradable plastics are plastics which are capable of degradation when they are attacked by microorganisms in natural or artificial conditions whereby the molar mass of degraded biodegradable plastics are reduced and hence can be transported into the microorganisms and fed into the appropriate metabolic pathways. As a result, the end-products of these metabolic processes include water and carbon dioxide ($CO_2$) together with newly producing biomass. A good example of biodegradable plastic is polylactide or poly Lactic acid (PLA). PLA can be produced by polymerization of bacterial fermented lactic acid and is claimed to be free from using of non-renewable source and to solve the environment problems. Therefore, PLA has rapidly become a focus of attention as a material alternative to existing plastics or fibers that are made from petroleum route. Another example biodegradable plastic is Poly (butylene Succinate) (PBS).

Indeed, currently available biodegradable resins require the addition of polymer additives such as color concentrate or pigment to enable their applications. Attempts have been made to process color concentrate on standard equipment and using known technologies in the plastic industry. For example, U.S. Pat. No. 8,133,558 discloses a method for producing PLA blown film composed of 1-20% of Titanium oxide ($TiO_2$) to develop its special colors. U.S. Pat. No. 7,273,896 discloses a method to visualize medical biomaterials from polysaccharide by using Fluorescein. U.S. Pat. No. 7,687,568 discloses a process of producing a polyester colorant concentrate by using carbon black pigment, Monoazo pigment, Disazo pigment, Phthalocyanine pigment, Anthraquinone pigment or Quinacridone pigment.

None of the above mentioned patents teach or suggest a method of production of biodegradable product which is made completely of bio-based materials. All of the colorant additive materials described in those patents are derived from non-renewable resources which cause much more serious environment problems because those molecules, such as fluorecein, are toxic to human as they disperse into the surrounding once the biodegradation process of the resin has occurred.

On the other hand, natural colorants wherein the main components or materials derived from natural products and/or their by-products offer an effective solution in eliminating or diminishing pollution on the earth. For example, U.S. Pat. No. 5,205,863 discloses a method for producing bio-plastic from starch acetate (starch acetate polymer) using 1% of red natural pigment from berry fruit as colorant additives. However, this method generates at least two new problems. First, the above production faces difficulties in controlling quality of raw material, especially controlling the color of fruit, because color in the fruits depends on climate and physical parameters such as light intensity, water supply, nutrient in soils, etc. Second, the security of raw material becomes to be issue because huge amount of those fruits are required and this may directly affect the human food supply. Therefore, the commercial production according to this method is almost impossible.

SUMMARY OF THE INVENTION

The present inventors have addressed the problems in the prior art and provide bio-based polymer additives prepared from biomass of microorganism cells, including biomass collected from natural resources, bioreactors or fermenters or waste from microorganism biomass as a sustainable solution to the problems and better utilization and disposal of waste from microorganism biomass. There are also provided biodegradable polymer compositions comprising the bio-based polymer additive prepared from the biomass of microorganism cells.

Accordingly, there is provided a bio-based polymer additive for use in manufacturing of biodegradable polymer. The bio-based polymer additive is prepared from the biomass of broken microorganism cell. There is also provided a biodegradable polymer composition comprising a biodegradable polymer and a bio-based polymer additive prepared from the biomass of broken microorganism cell according to the invention. In particular, the bio-based polymer additive of any aspect of the invention is in powder form obtained from powdering the biomass of microorganism broken cells or by concentrating the biomass solution.

According to a particular aspect of the invention, the microorganism cell of the microorganism biomass comprises one or more color molecules. According to this aspect, the bio-based polymer additive according to the invention is for use as a pigment. Accordingly, the bio-based polymer additive according to the invention comprises or is a bio-based polymer additive pigment. Therefore, there are also provided biodegradable plastics comprising the bio-based additive of the invention which are made completely of natural colorant wherein the component or material used is derived from a product of advance agricultural or biotechnological industries such as microorganism biomass, in which the ease of mass production and quality control take place, and hence make it very economically viable. According to this aspect, the bio-based polymer additive according to the invention may be for use as colorant. In the present invention, microorganism biomasses containing color molecules from several biotechnological industries are used as natural pigment.

In the bio-based polymer additive according to any aspect of the invention, the microorganism of the biomass may be selected from microalgae, yeast, and bacteria or a mixture thereof. In particular, the microorganism may be selected from Division of Cyanophyta, Prochlorophyta, Rhodophyta, Chlorophyta, Dinophyta, Chrysophyta, Prymnesiophyta, Bacillariophyta, Xanthophyta, Eustigmatophyta, Rhaphidophyta, Phaeophyta, Proteobacteria, Cyanobacteria, Eubacteria, Spirochetes, Chlamydiae, Zygomycota or Eumycota or combination thereof.

In particular, in the biodegradable polymer composition comprising a biodegradable polymer and a bio-based polymer additive (for example, for use as a pigment) prepared from the biomass of broken microorganism cell according to the invention, the bio-based polymer additive ranges from 0.05 to 10% by weight. More in particular, the bio-based polymer additive ranges from 0.5 to 5% by weight.

The biodegradable polymer may be any biodegradable polymer suitable for the purposes of any aspect of the invention. In particular, the biodegradable material may be selected from biodegradable polyesters, such as poly(butylene succinate) (PBS) and/or polylactic acid (PLA).

The biodegradable polymer compositions according to the present invention provide enhanced rheological properties, as compared to a non-additive containing biodegradable polymer composition. The biodegradable polymer composition according to the invention also provides enhanced biodegradability properties, as compared to a non-additive containing biodegradable polymer composition.

Accordingly, there is also provided a method of enhancing the rheological properties of a polymer, comprising adding a bio-based polymer additive according to any aspect of the invention to a polymer. There is also provided a method of enhancing the biodegradability property of a biodegradable polymer, comprising adding a bio-based polymer additive according to any aspect of the invention to a biodegradable polymer. In addition, when the bio-based polymer additive is a bio-based polymer additive pigment, the invention also provides a method for coloring a polymer, comprising adding a bio-based polymer additive pigment according to the invention to a polymer.

There is also provided a process for producing a bio-based polymer additive, the process comprising the steps of:
a) providing microorganism biomass; and
b) breaking microorganism cell of the biomass obtained from a).

In particular, the process of producing the bio-based polymer additive may further comprise a step c) of powdering the biomass of broken microorganism cell obtained from step b). The powdering may selected from a hot powdering method or cold powdering method. The hot powdering method may be selected from a spray drying, evaporation, rotary drying, flash drying, disk drying, cascade drying, superheated steam drying. The cold powdering method may be selected from a freeze drying, spray congealing or spray cooling. Alternatively, the step c) may comprise concentrating the biomass of broken microorganism cell obtained from step b).

The microorganism biomass of step a) may be obtained by collecting it from natural resources, bioreactors or fermenters. In particular, the microorganism biomass may be added in aqueous solution at solid concentration of 50 to 200 gram per liter. In particular, the step b) of the process may be a mechanical cell breaking method carried out at temperature of 20 to 80° C. The mechanical cell breaking method may be selected from a homogenization method, sonication method, freeze-thaw method, mortar and pestle method or ultrasonic method.

There is also provided an article of manufacture prepared with the biodegradable polymer composition according to any aspect of the invention.

BRIEF DESCRIPTION OF DRAWINGS

This patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
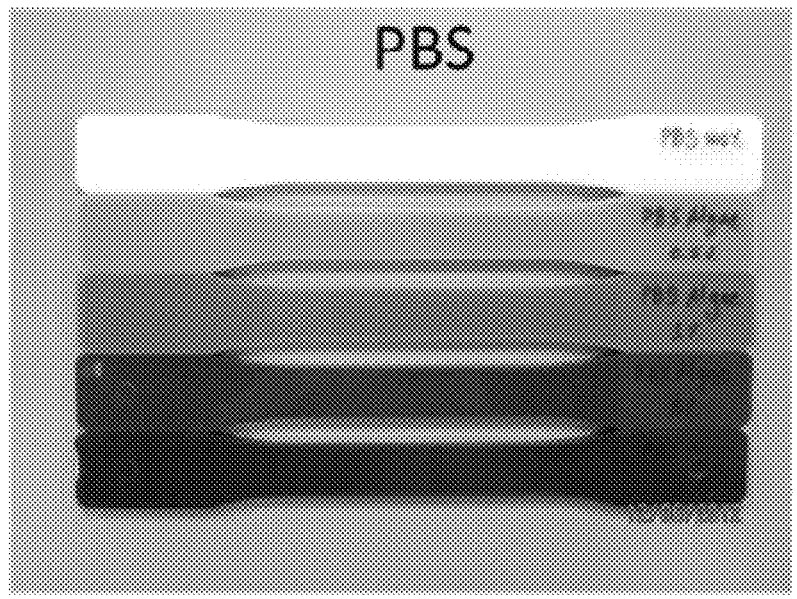
FIG. 1 is an image of biodegradable resin (PBS) introduced with bio-based polymer additive pigment from microalgae biomass powder in several ratios.

Any aspects shown here are also intended to include any applications to any other aspects of this invention, unless stated otherwise.

Technical terms and scientific terms used herein have definitions as understood by those having an ordinary skill in the art, unless stated otherwise.

The use of singular noun or pronoun when used with the term "comprising" in the claims and/or specification means "one", and also includes "one or more", "at least one", and "one or more than one".

The term "microorganism biomass" as used herein refers to biomasses derived from microorganisms, which are derived from biotechnological industries including biomass of microorganism. The microorganism according to the invention may be microalgae, yeast and/or bacteria. Other microorganism suitable to the invention may also be used. The microorganism biomass can be collected from natural resources, bioreactors or fermenters, or part of solid wastes from biotechnological industry, for example, brewer's yeast, *Saccharomyces cerevisiae*, after the production of ethanol in a fermentation process. Throughout this application, any type of microorganism may refer to unicellular form, multicellular form or both.

The terms "microorganism cell comprising additive pigment" or "microorganism cell comprising color pigment" as used herein refers to microorganism cells, for example microalgae, yeast, and/or bacteria, which comprise natural color pigment molecules. For example, the color molecule may be selected from anthocyanins, chlorophylls, carotenoids and phycobilins, or a mixer thereof.

The term "bio-based polymer additive" as used herein refers to additive(s) obtained from breaking cells of microorganism biomass.

The term "bio-based polymer additive pigment" as used herein refers to additive pigment(s) obtained from breaking cells of microorganism biomass, wherein the microorganism cells comprise color molecules.

The term "pigment" as used herein refers either an insoluble or a soluble color particle.

The term "biodegradable polymer composition" as used herein refers to a composition comprising at least one biodegradable polymer and at least one bio-based polymer additive, for example a bio-based polymer additive pigment, according to the invention.

Throughout this application, the term "about" used to identify any values shown or appeared herein may be varied or deviated. The variation or deviation may be caused by errors of devices and methods used to determine a variety of values.

The terms "comprise", "have", and "include" are open-ended linking verbs. One or more forms of these verbs such as "comprise", "which comprise", "have", "which have", "include", "which include" are also open-ended. For example, any methods, which "comprise", "have", or "include" one or more steps, are not limited to possess only the one or those more steps, but also cover all unidentified steps.

Any instruments, equipment, methods or reagents mentioned herein, unless indicated otherwise, shall mean instruments, equipment, methods or reagents that are generally used or practiced by a person skilled in the art of this field.

Microorganisms are important tools in the biotechnological industry. Several developments of microorganism cultivation in bio-reactors have been happening for a long time. For example, a brewer yeast *Saccharomyces cerevisiae* plays a key role in ethanol production via a fermentation process in which the by-products are important not only in the beverage production but also as an alternative energy supply for the automobile industry. After the purification of ethanol from the fermentor, yeast biomass is regarded as a by-product or waste. It is known that *S. cerevisiae* biomass contains the red color molecule, anthocyanin, and can be used as colorant. Therefore, large amounts of *S. cerevisiae* yeast biomass are considered by-products or waste from those ethanol production factories and can be used as natural colorant.

Algae production for food and food additive applications is well known. In recent years, microalgae have come into the spotlight of the biofuel industry as several species are known to produce oils and lipids. With biomass fractionation followed by transesterification with methanol, this will result in the formation of biodiesel. Microalgae have therefore been proposed as excellent candidates for fuel production because of their combined advantages of high-photosynthetic efficiency, biomass production and faster growth, as compared to other energy crops. Furthermore, as these organisms can grow photoautotrophically, their simple growth requirements make them well-suited for growth in large-scale photobioreactors for the industrial-scale production of biofuel in the twenty first century.

Microalgae contain organic pigments for harvesting light energy. There are three major classes of pigments: chlorophylls, carotenoids and phycobilins. The chlorophylls (green pigments) and carotenoids (yellow or orange pigments) are lipophilic and associated in Chl-protein complexes, while phycobilins are hydrophilic. Chlorophyll molecules consist of a tetrapyrrole ring containing a central magnesium atom, and a long-chain terpenoid alcohol. Structurally, the various types of Chlorophyll molecules designated a, b, c and d differ in their side-group substituents on the tetrapyrrole ring. All chlorophyll molecules have two major absorption bands: blue or blue-green (450-475 nm) and red (630-675 nm).

Chlorophyll a is represented in all oxygenic photoautotrophs as a part of core and reaction center pigment protein complexes, and in light-harvesting antennae it is accompanied by chlorophyll b or chlorophyll c.

Carotenoids represent a large group of biological chromophores with an absorption range between 400 and 550 nm. The basic structural elements of carotenoids are two hexacarbon rings joined by an 18-carbon, conjugated double-bond chain. They are usually either hydrocarbons (carotenes, e.g. alpha-carotene, beta-carotene) or oxygenated hydrocarbons (xanthophylls, e.g. lutein, violaxanthin, zeaxanthin, fucoxanthin, peridinin).

Carotenoids have several roles in the photosynthetic apparatus, functioning as (1) accessory light-harvesting pigments transferring excitation to Chl a, (2) structural entities within the light-harvesting and reaction centre pigment-protein complexes; and (3) molecules required in the protection against excess irradiance, chlorophyll triplets and reactive oxygen species.

In cyanobacteria such as *Spirulina* sp. and red algae, the major antennae contain phycobilins, e.g. phycoerythrobilin, phycocyanobilin and phycourobilin. These accessory pigments absorb blue-green, green, yellow, or orange light (500-650 nm). Phycobiliproteins are water-soluble and the pigments are, covalently bound to apoprotein.

In the present invention, microalgae may be selected from the prokaryotic algae in Division Cyanophyta and Division Prochlorophyta or eukaryotic algae in Division Rhodophyta, Division Chlorophyta, Division Dinophyta, Division Chrysophyta, Division Prymnesiophyta, Division Bacillariophyta, Division Xanthophyta, Division Eustigmatophyta, Division Rhaphidophyta and Division Phaeophyta. Examples of prokaryotic algae are *Spirulina* sp. which is cyanobacteria from Division Cyanophyta containing chlorophyll, phycocyanin, Phycoerythrin, beta-carotene, beta-cryptoxanthin and Zeaxanthin. An example of eukaryotic algae is *Nannochloropsis* sp. in Division Eustigmatophyta.

In the present invention, the microorganism may be selected from prokaryotic microorganisms which contain the color molecules in Division (Phylum) Proteobacteria, Division (Phylum) Cyanobacteria, Division (Phylum) Eubacteria, Division (Phylum) Spirochetes and Division (Phylum) Chlamydiae.

In the present invention, the microorganism may be selected from eukaryotic microorganisms which contain the color molecules in Division Zygomycota, Division Eumycota, for example, *S. cerevisiae* which contains the red color molecule of anthocyanin.

In one aspect, the present invention provides a bio-based polymer additive for use in a manufacturing of a biodegradable polymer composition. The bio-based polymer additive is prepared from biomass of broken microorganism cell.

In the bio-based polymer additive according to any aspect of the invention, the microorganism of the biomass may be selected from microalgae, yeast, and bacteria or a mixture thereof. In particular, the biomass may be selected from Division of Cyanophyta, Division Prochlorophyta, Division Rhodophyta, Division Chlorophyta, Division Dinophyta, Division Chrysophyta, Division Prymnesiophyta, Division Bacillariophyta, Division Xanthophyta, Division Eustigmatophyta, Division Rhaphidophyta, Division Phaeophyta, Division Proteobacteria, Division Cyanobacteria, Division Eubacteria, Division Spirochetes, Division Chlamydiae, Division Zygomycota or Division Eumycota, or combination thereof. More particularly, the biomass is selected from microalgae biomass or yeast biomass or combination thereof.

In another aspect of the invention, the invention provides biodegradable polymer composition comprising a biodegradable polymer and a bio-based polymer additive prepared from the biomass of broken microorganism cell. More preferably, the bio-based polymer additive is ranging from 0.05 to 10% by weight. Most preferably, the bio-based polymer additive is ranging from 0.5 to 5% by weight. Any biodegradable polymer suitable to the purpose of any aspect of the present invention may be used. The biodegradable polymer may be selected from biodegradable polyesters. For example, the biodegradable polyester may be, but not limited to, poly(butylene succinate) (PBS) or polylactic acid (PLA) or a mixture therefrom.

It is important to note that compared to unbroken microorganism cells, broken microorganism cells of the biomass provide more compatibility of biodegradable polymer and bio-based additive, and therefore enhance the properties and characteristics, including color properties, of biodegradable polymer composition produced therefrom. In particular, the use of the composition comprising a biodegradable polymer and the bio-based polymer additive prepared from microorganism biomass of broken microorganism cell according to the present invention, the biodegradable polymer can be mixed efficiently with the additive without the addition of a compatibility agent, for example an oil, as a way to enhance mixing efficiency. Accordingly, it is suggested that the step of breaking the microorganism cells in important to prepare the micro-organism-derived bio-based polymer additives, without the addition of further additives (different from the bio-based polymer additives according to the invention).

In known methods in the prior art, microorganisms are in general first dried and then grinded. On the contrary, in the process of the invention microorganism cells are first broken and then treated for the preparation of the additive, for example by a drying step or a solution concentrating step. In particular, the present inventors have found that breaking the cells before the step of drying or concentrating is an advantage since the cell wall and/or cell membranes are destroyed and then the additive molecules, for the example the additive pigment molecules, are able to expose outside of the cell. On the other hand, the step of drying before breaking the cells cause the dehydration of water in the cell without the disruption of the cell wall/membrane. The result is that the additive (including the pigment) molecules are trapped into the dried cells so that the release of the additive (including the pigment) molecule from the dried cell is difficult.

Yet another aspect of the invention, the invention relates to a process for producing a bio-based polymer additive, the process comprising the steps of:
 a) providing microorganism biomass; and
 b) breaking microorganism cell of the biomass obtained from a).

Step a) may comprise harvesting microalgae or other color molecules containing microorganisms from a natural lake or lagoon, open pond, closed-photobioreactor. The microorganism biomass of step a) may be obtained by collecting it from natural resources, bioreactors or fermenters. In particular, the microorganism biomass may be added in aqueous solution at solid concentration of 50 to 200 gram per liter. In particular, the step b) of the process may be a mechanical cell breaking method carried out at temperature of 20 to 80° C. The mechanical cell breaking method may be selected from a homogenization method, sonication method, freeze-thaw method, mortar and pestle method or ultrasonic method.

In particular, the process of producing the bio-based polymer additive may further comprise a step c) of powdering the biomass of broken microorganism cell obtained from b). The powdering may be selected from a hot powdering method or cold powdering method. The hot powdering method may be selected from a spray drying, evaporation, rotary drying, flash drying, disk drying, cascade drying, superheated steam drying. The cold powdering method may be selected from a freeze drying, spray congealing or spray cooling.

Alternatively, in step c) the preparation of the additive may be obtained with methods different from powdering. For example, the additive can be prepared by concentrating the biomass of broken microorganism cells. More in particular, the step comprises concentrating the biomass of broken microorganism cells and then dispersing to an appropriate liquid carrier that is compatible with the resin (polymer) being processed. More in particular, according to this alternative step c), the additive may be obtained by mixing water comprising concentrated pigment dispersions with an aromatic hydrocarbon in an amount necessary to remove the water in the dispersion completely by azeotropic distillation. Then, the resulting homogeneous slurry may be heated at temperature equal to or lower than 90° C. under reduced pressure to remove the residual water and the added aromatic hydrocarbon and the lower alcohol as an azeotropic mixture.

According to an aspect of the invention, the present invention provides a bio-based polymer additive for use in a manufacturing of the production of biodegradable polymer composition. The bio-based polymer additive is prepared from biomass of broken microorganism cell. The said biomass is obtained from or derived as solid biomass of microorganism selected from Division of Cyanophyta, Prochlorophyta, Rhodophyta, Chlorophyta, Dinophyta, Chrysophyta, Prymnesiophyta, Bacillariophyta, Xanthophyta, Eustigmatophyta, Rhaphidophyta, Phaeophyta, Proteobacteria, Cyanobacteria, Eubacteria, Spirochetes, Chlamydiae, Zygomycota or Eumycota, or combination thereof. In particular, said biomass is selected from microalgae or yeast or combination thereof. More in particular, said microalgae biomass is selected from *Spirulina* while said yeast biomass is selected from *Saccharomyces*. The additive according to the invention may be prepared as described above, that is, comprising the steps of:
 a) providing microorganism biomass; and
 b) breaking microorganism cell of the biomass obtained from a).

Further, the process may comprise a step c) of powdering the biomass of broken microorganism cell obtained from b). Alternatively, the step c) may comprise concentrating the biomass of broken microorganism cells.

According to a particular embodiment of the present invention, the bio-based polymer additive from microorganism biomass according to the present invention may be prepared from a process comprising of the following steps:
 a) obtaining microorganism biomass, the microorganism biomass may be obtained from collecting biomass of microorganism which is discarded as by-product waste from the biotechnological industries, which usually come in a form of solid waste. It is also possible that the biomass may be harvested from natural resources, such as natural lake, lagoon, open pond, or from cultured plant/reactor, bioreactors or fermenters.
 b) breaking microorganism cell of the biomass obtained from a), as an exemplary embodiment, the biomass obtained from a) may be diluted in an aqueous solution to obtain a mixture of dried biomass with a predetermined quantity amount of biomass. In an exemplary embodiment, the amount of biomass in solid concentration is 50 to 200 gram per liter. The mixture of biomass is then under mechanically cell breaking at a temperature of 20 to 80° C. The mechanical cell breaking method may be selected from a homogenization method, sonication method, freeze-thaw method, mortar and pestle method or ultrasonic method.
 c) powdering the biomass of broken microorganism cell obtained from b), the mixture of broken microorganism cell from the step b) is diluted in an aqueous solution and then dried to obtain powdered bio-based polymer additive. In this step, the powdering process may be performed by using hot or cold powdering methods, the hot powdering methods such as spray drying, evaporation, rotary drying, flash drying, disk drying, cascade drying or superheated steam drying, and the cold powdering methods such as freeze drying, spray congealing or spray cooling.

The biodegradable polymer compositions according to the present invention provide enhanced rheological properties, as compared to a non-additive containing biodegradable polymer composition. The biodegradable polymer composition according to the invention also provides enhanced biodegradability properties, as compared to a non-additive containing biodegradable polymer composition.

Accordingly, there is also provided a method of enhancing the rheological properties of a polymer, comprising adding a bio-based polymer additive according to any aspect of the invention to a polymer. There is also provided a method of enhancing the biodegradability property of a biodegradable polymer, comprising adding a bio-based polymer additive according to any aspect of the invention to a biodegradable polymer.

According to a particular aspect of the invention, the microorganism cell of the microorganism biomass comprises one or more color molecules. According to this aspect, the bio-based polymer additive according to the invention is for use as a pigment, in particular, for coloring biodegradable polymers. Accordingly, the bio-based polymer additive according to this aspect of the invention may comprise or is a bio-based polymer additive pigment. Accordingly, there are provided biodegradable plastics comprising bio-based additive (pigment) which are made completely of natural colorant wherein the component or material used is derived from a product of advance agricultural or biotechnological industries such as microorganism biomass, in which the ease of mass production and quality control take place, and hence make it very economically viable. According to this aspect, the bio-based polymer additive according to the invention may be for use as colorant.

In particular, there is provided a bio-based polymer additive pigment, for use as colorant in manufacturing of biodegradable polymer, wherein the additive pigment is from the biomass of broken microorganism cells.

In the bio-based polymer additive for use as pigment according to any aspect of the invention, the microorganism of the biomass may be selected from microalgae, yeast, and bacteria or a mixture thereof.

In particular, the microorganism may be selected from Division of Cyanophyta, Prochlorophyta, Rhodophyta, Chlorophyta, Dinophyta, Chrysophyta, Prymnesiophyta, Bacillariophyta, Xanthophyta, Eustigmatophyta, Rhaphidophyta, Phaeophyta, Proteobacteria, Cyanobacteria, Eubacteria, Spirochetes, Chlamydiae, Zygomycota or Eumycota or combination thereof.

The color molecule may be selected from anthocyanins, chlorophylls, carotenoids including carotenes, e.g. alpha-carotene, beta-carotene or oxygenated hydrocarbons xanthophylls, e.g. lutein, violaxanthin, zeaxanthin, fucoxanthin, peridinin, betalains, porphyrins phycobilins, or a mixer thereof.

There is also provided a biodegradable polymer composition comprising a biodegradable polymer and a bio-based polymer additive, for use as a pigment, prepared from the biomass of broken microorganism cell according to the invention. The bio-based polymer additive ranges from 0.05 to 10% by weight. More in particular, the bio-based polymer additive ranges from 0.5 to 5% by weight.

The biodegradable polymer may be any biodegradable polymer suitable for the purposes of any aspect of the invention. In particular, the biodegradable material may be selected from biodegradable polyesters, such as poly(butylene succinate) (PBS) and/or polylactic acid (PLA).

In addition to the properties already described for the bio-based polymer additive and biodegradable polymer composition comprising the bio-based polymer additive according to the invention, when the bio-based polymer additive is a bio-based polymer additive pigment, the invention also provides a method for coloring a polymer, comprising adding a bio-based polymer additive pigment according to the invention to a polymer.

There is also provided an article of manufacture prepared with the biodegradable polymer composition according to any aspect of the invention.

The method for preparation of bio-based polymer additive according to the principle of the invention described above will now be discussed in details with examples. The particulars of the invention shown herein are by way of example. They are meant to illustrate various embodiments of the invention and not meant to limit the principles or concepts of the invention.

EXAMPLE 1

Preparation of Bio-based Polymer Additive Pigment from Microalgae Biomass

The following example is aimed to prepare the green bio-based additive pigment from microalgae *Spirulina* biomass.

Microalgae *Spirulina* cells, harvested from closed-bioreactor, were obtained. The cells were then added to deionized water to generate a mixture with concentration of 200 g dried cell per liter. The *Spirulina* cells in the mixture were subsequently mechanically broken by using a homogenizer with 10,000 rpm for 30 minutes, during which the temperature was maintained to be about below 80° C. The mixture resulting from the breaking of the *Spirulina* cells was diluted by deionized water to generate a mixture with concentration of 50 g dried cell per liter.

Then, the mixture was dried at about 160° C. with a feeding rate 0.3 L/h to obtain microalgae-derived polymer additive pigment powder. The particle size of the obtained microalgae-derived polymer additive pigment powder was determined by Particle size analyzer-Malvern Instrument (Mastersizer 2000). The average distribution of the particles was between about 6-9 microns.

EXAMPLE 2

Preparation of Bio-based Polymer Additive Pigment from Yeast Biomass

It is known that yeast *Saccharomyces* biomass contains the red-orange color molecule, anthocyanin in the cell. The following example is aimed to prepare the red-orange bio-based additive pigment from yeast *Saccharomyces* biomass.

Yeast, *Saccharomyces* biomass was obtained from fermentor. The cells were then added to deionized water to generate a mixture with concentration of 200 g dried cell per liter. *Saccharomyces* cells in the mixture were subsequently mechanically broken by using a homogenizer with 10,000 rpm for 30 minutes during which the temperature is maintained to be about below 80° C. The mixture resulting from the breaking of the *Saccharomyces* cells was diluted by deionized water to generate a mixture with a concentration of 50 g dried cell per liter. Then, the mixture was dried at temperature about 160° C. at a feeding rate about 0.3 L/h to obtain a yeast-derived polymer additive pigment powder. The particle size of the yeast-derived polymer additive pigment powder was determined by Particle size analyzer-Malvern Instrument (Mastersizer 2000). The average distribution of the particles was between about 6-9 microns.

Turning now to another aspect of the invention, the invention discloses a biodegradable polymer composition comprising a biodegradable polymer and a bio-based polymer additive for use in the production of biodegradable polymer. The bio-based polymer additive is prepared according to the process as described above.

The biodegradable polymer composition according to the exemplary embodiment of the present invention comprising a biodegradable polymer selected from biodegradable polyesters, preferably, from polylactic acid (PLA) or poly(butylene succinate) (PBS), and a bio-based polymer additive prepared from the process as described in this invention.

In an embodiment, the biodegradable polymer composition according to the present invention comprising biodegradable polymer selected from biodegradable polyesters, such as polylactic acid (PLA) or poly(butylene succinate) (PBS), and a bio-based polymer additive ranging from about 0.05 to 10% by weight.

In an embodiment, the biodegradable polymer composition according to the present invention comprising biodegradable polymer selected from biodegradable polyesters, such as polylactic acid (PLA) or poly(butylene succinate) (PBS), and a bio-based polymer additive ranging from about 0.5 to 5% by weight.

In an embodiment, the biodegradable polymer composition comprising PBS and a bio-based polymer additive prepared from microalgae biomass selected from *Spirulina* wherein the additive is ranging from about 0.5 to 5% by weight.

In an embodiment, the biodegradable polymer composition comprising PLA and a bio-based polymer additive prepared from microalgae biomass selected from *Spirulina* wherein the additive is ranging from about 0.5 to 5% by weight.

In an embodiment, the biodegradable polymer composition comprising PBS and a bio-based polymer additive prepared from yeast biomass selected from *Saccharomyces* wherein the additive is ranging from about 0.5 to 5% by weight In an embodiment, the biodegradable polymer composition comprising PLA and a bio-based polymer additive prepared from yeast biomass selected from *Saccharomyces* wherein the additive is ranging from about 0.5 to 5% by weight.

The biodegradable polymer composition according to the present invention may be prepared by a method commonly known by a person having skill in the art. The method may comprise the steps of:
  mixing biodegradable polymer to a bio-based polymer additive prepared according to the present invention at a predetermined ratio;
  extruding the mixture by feeding the mixture into an extruder at a predetermined feeding rate at which the screw of the extruder is heated at a predetermined temperature and the screw speed is set at a predetermined speed;
  cutting the extruded material into small piece
  injecting into a mold to obtain a molded specimen.

The biodegradable polymer composition according to the present invention may be produced using the method/process according to the following examples:

EXAMPLE 3

A Polymer Composition Comprising PBS and a Bio-based Polymer Additive Prepared from Microalgae Biomass In this example, Poly(butylene succinate) (PBS) FZ71PD from Mitsubishi Chemical Corporation was mixed with the bio-based polymer additive powder derived from Example 1 at the ratio of 0.5, 1.0, 3.0 and 5.0% by weight. The mixture was fed into an extruder, specifically an Extrusion Line and Mixer (Haake Rheometer Os), at a feeding rate of about 1.5 g per minute, in which the screw of the extruder was heated at about 170° C. and the screw speed was set at 120 RPM. The extruded polymer composition was then cut with the Haake Rheometer OS to reduce the size. The mixture was then made into a dumbbell-shaped specimen using injector EC100II2A (Toshiba) with a capacity of 61 kg/h. Injection was done under an injection pressure of 200 MPa, at a Barrel temperature of 165° C. and a mold temperature of 40° C. Then, the finished specimen (FIG. 1) was subjected to performance test.

EXAMPLE 4

Figure 2:
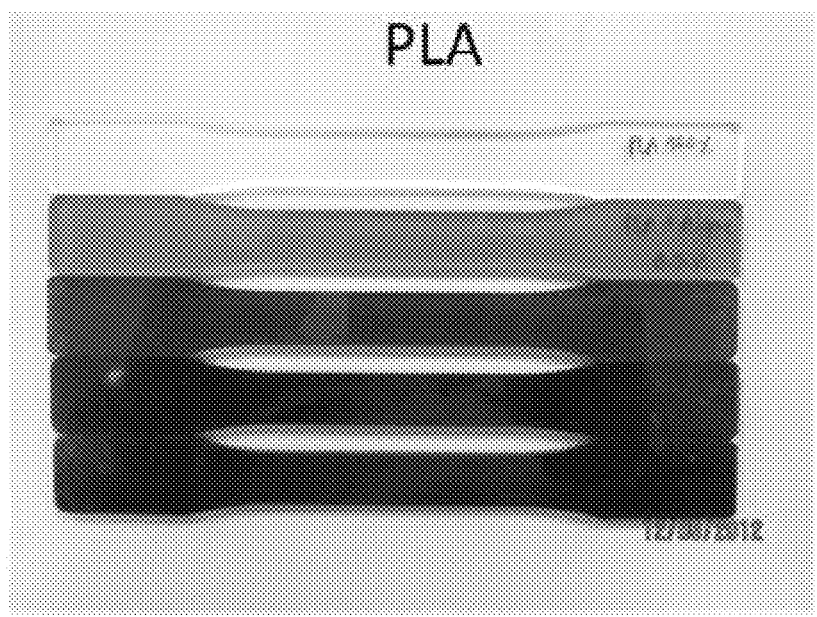
FIG. 2 is an image of biodegradable resin (PLA) introduced with bio-based polymer additive pigment from microalgae powder in several ratios.

A Polymer Composition Comprising PLA and a Bio-based Polymer Additive Prepared from Microalgae Biomass In this example, Poly Lactic Acid (PLA) 2002D from Naturework was mixed with the bio-based polymer additive powder prepared in accordance with Example 1 at the ratio of about 0.5, 1.0, 3.0 and 5.0% by weight. The mixture was fed into an extruder, specifically an Extrusion Line and Mixer (Haake Rheometer Os), at feeding rate 1.5 g per minute, in which the screw was heated at temperature about 170° C. and the screw speed was set at 120 RPM. The extruded polymer composition was then cut with the Haake Rheometer OS to reduce the size. The mixture was then made into a dumbbell-shaped specimen using injector EC100II2A (Toshiba) with a capacity of 61 kg/h. Injection was done under an injection pressure of 200 MPa, at a Barrel temperature of 165° C. and a mold temperature of 40° C. Then, the finished specimen (FIG. 2) was subjected to performance test.

EXAMPLE 5

Figure 3:
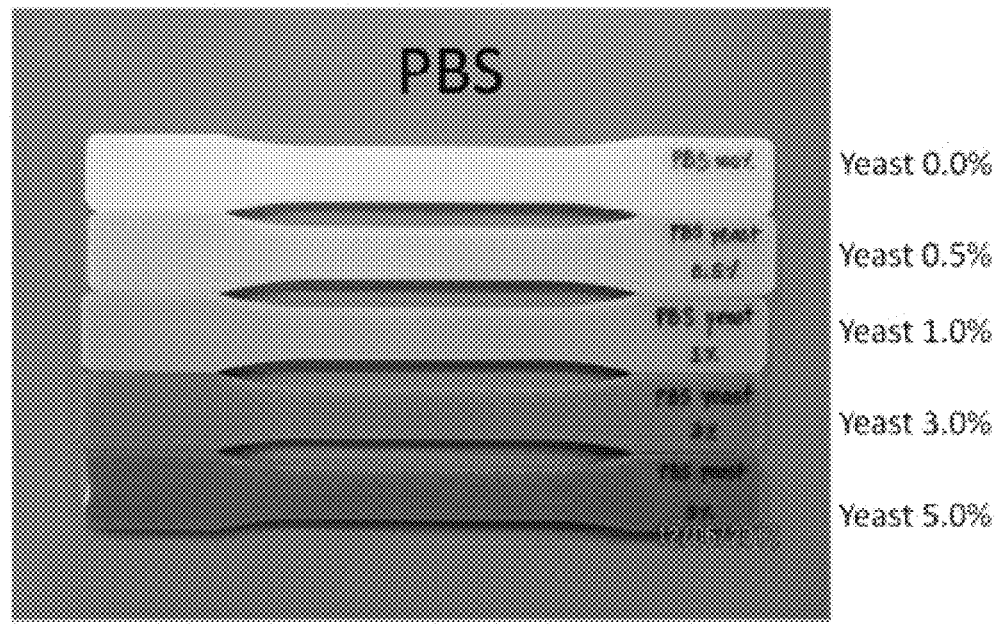
FIG. 3 is an image of biodegradable resin (PBS) introduced with bio-based polymer additive pigment from yeast powder in several ratios.

A Polymer Composition Comprising PBS and a Bio-based Polymer Additive Prepared from Yeast Biomass In this example, Poly(butylene succinate) (PBS) FZ71PD from Mitsubishi Chemical Corporation was mixed with the bio-based polymer additive prepared from yeast biomass of Example 2 at a ratio of 0.5, 1.0, 3.0 and 5.0% by weight. The mixed material was then fed into an extruder, specifically an Extrusion Line and Mixer (Haake Rheometer Os), at feeding rate 1.5 g per minute, in which a screw was heated at temperature about 170° C. and the screw speed was set at 120 RPM. The extruded polymer composition was then cut with the Haake Rheometer OS to reduce the size. The mixture was then made into a dumbbell-shaped specimen using injector EC100II2A (Toshiba) with a capacity of 61 kg/h. Injection was done under an injection pressure of 200 MPa, at a Barrel temperature of 165° C. and a mold temperature of 40° C. Then, the finished specimen (FIG. 3) was subjected to performance test.

EXAMPLE 6

Figure 4:
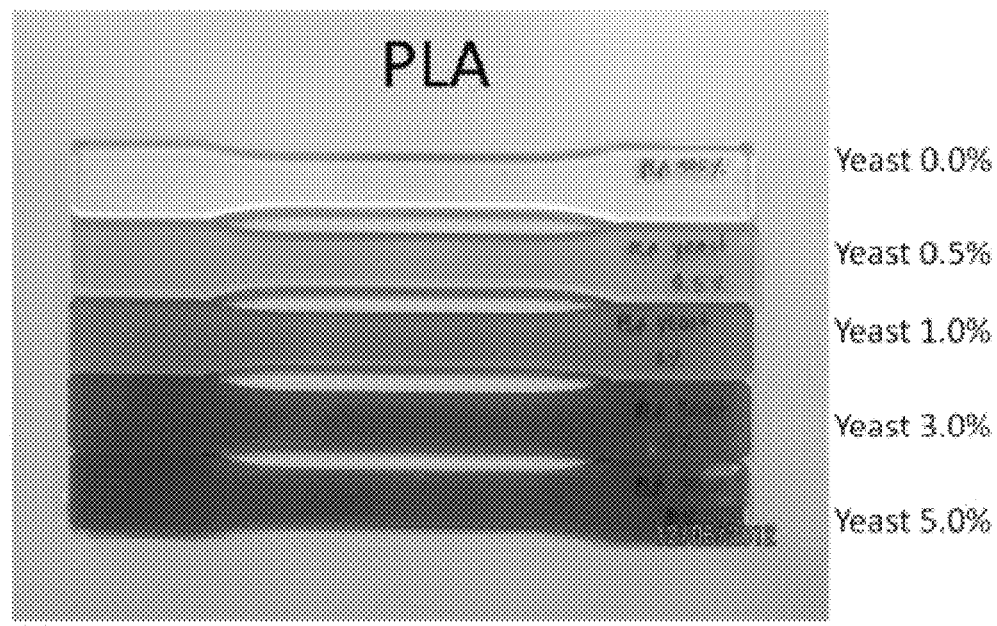
FIG. 4 is an image of biodegradable resin (PLA) introduced with bio-based additive pigment from yeast powder in several ratios.
Figure 5:
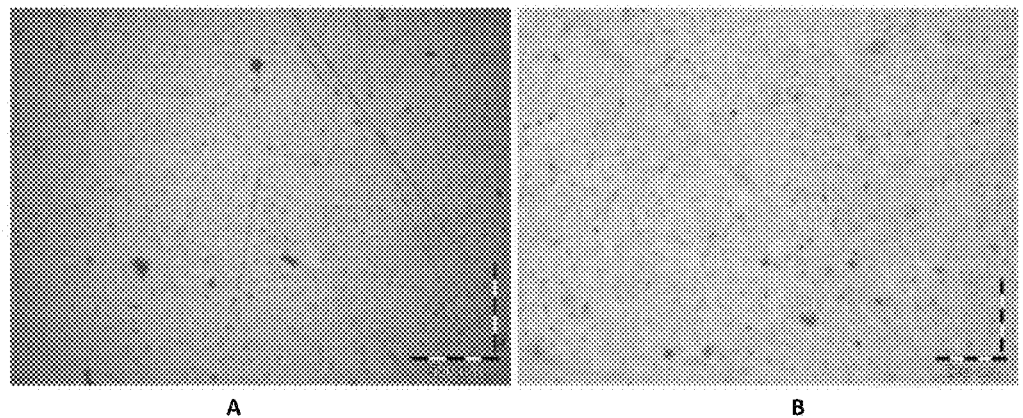
FIG. 5 illustrates an optical microscopic photograph showing biodegradable polymer, which is poly(butylene succinate) (PBS) introduced with a bio-based polymer additive prepared from microalgae biomass at a ratio of 1.0% taken at 500× (Left)(A) and 1000× (Right)(B).
Figure 6:
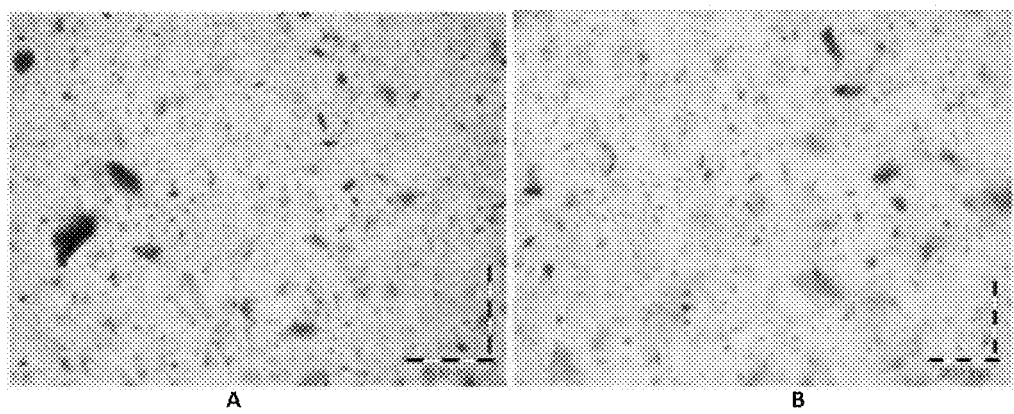
FIG. 6 illustrates an optical microscopic photograph showing biodegradable polymer, which is poly(butylene succinate) (PBS) introduced with a bio-based polymer additive prepared from microalgae biomass at a ratio of 5.0% taken at 500× (Left) (A) and 1000× (Right)(B).
Figure 7:
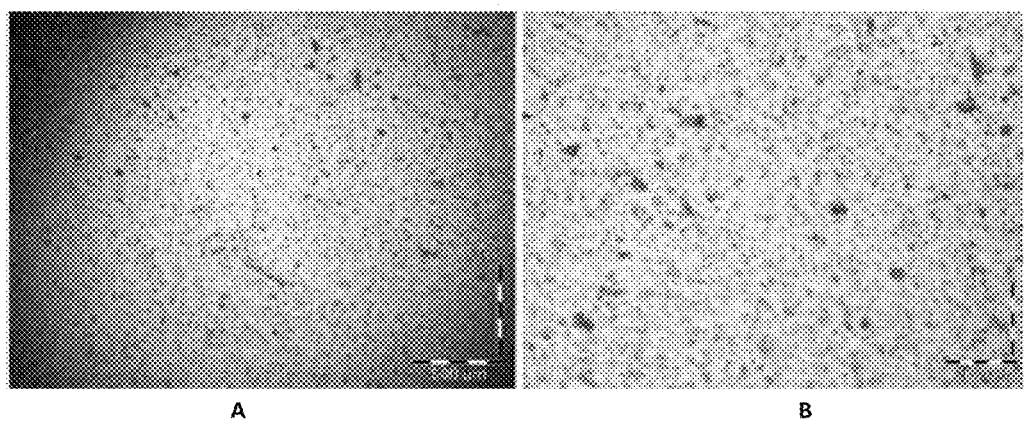
FIG. 7 illustrates an optical microscopic photograph showing biodegradable polymer, which is polylactic acid (PLA) introduced with a bio-based polymer additive prepared from microalgae biomass at a ratio of 1.0% taken at 500× (Left)(A) and 1000× (Right)(B).
Figure 8:
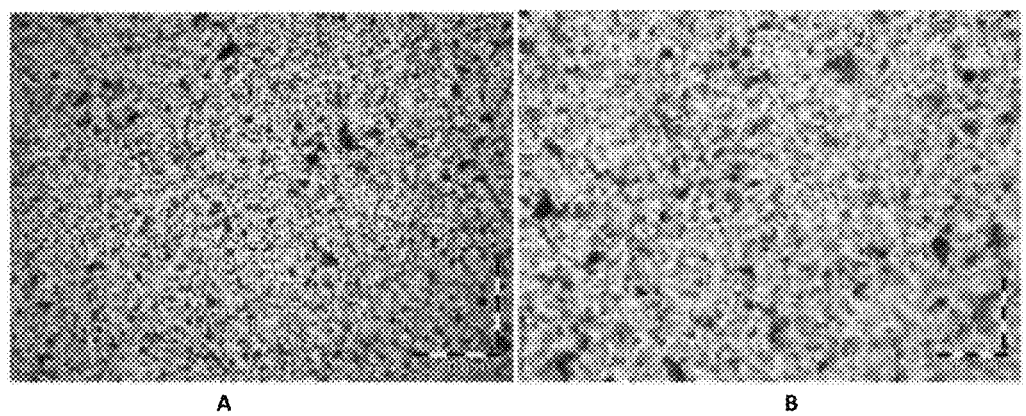
FIG. 8 illustrates an optical microscopic photograph showing biodegradable polymer, which is polylactic acid (PLA) introduced with a bio-based polymer additive prepared from microalgae biomass at a ratio of 5.0% taken at 500× (Left)(A) and 1000× (Right)(B).
Figure 9:
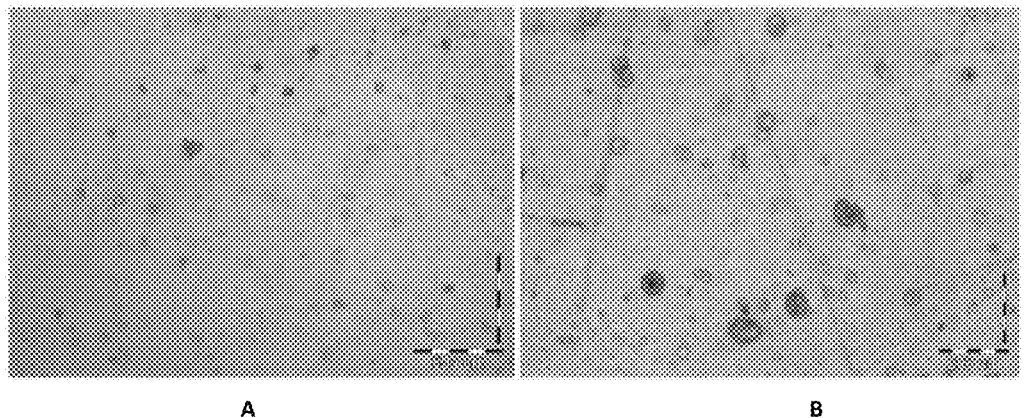
FIG. 9 illustrates an optical microscopic photograph showing biodegradable polymer, which is poly(butylene succinate) (PBS) introduced with a bio-based polymer additive prepared from yeast biomass at a ratio of 1.0% taken at 500× (Left)(A) and 1000× (Right)(B).
Figure 10:
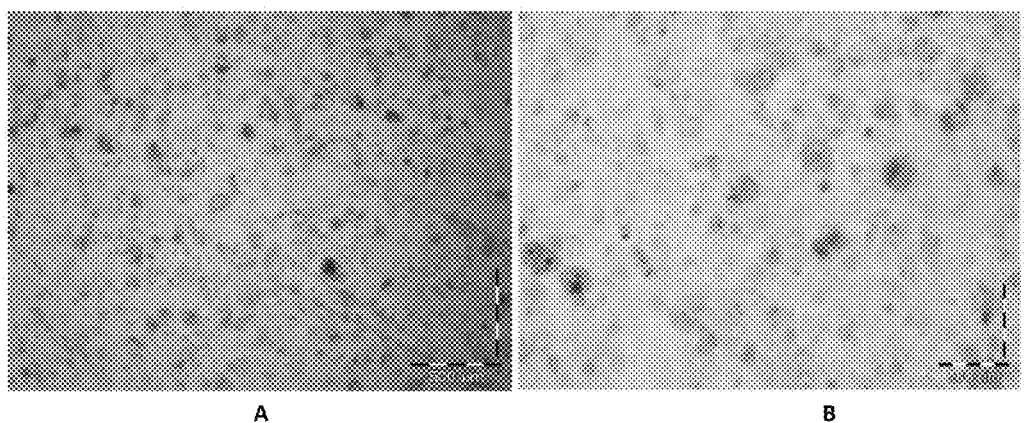
FIG. 10 illustrates an optical microscopic photograph showing biodegradable polymer, which is poly(butylene succinate) (PBS) introduced with a bio-based polymer additive prepared from yeast biomass at a ratio of 5.0% taken at 500× (Left)(A) and 1000× (Right)(B).
Figure 11:
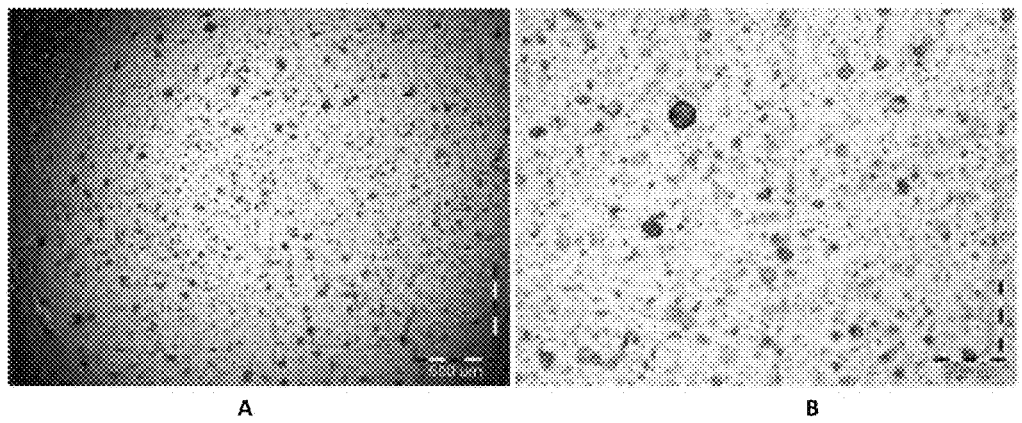
FIG. 11 illustrates an optical microscopic photograph showing biodegradable polymer, which is polylactic acid (PLA) introduced with a bio-based polymer additive prepared from yeast biomass at a ratio of 1.0% taken at 500× (Left)(A) and 1000× (Right)(B).
Figure 12:
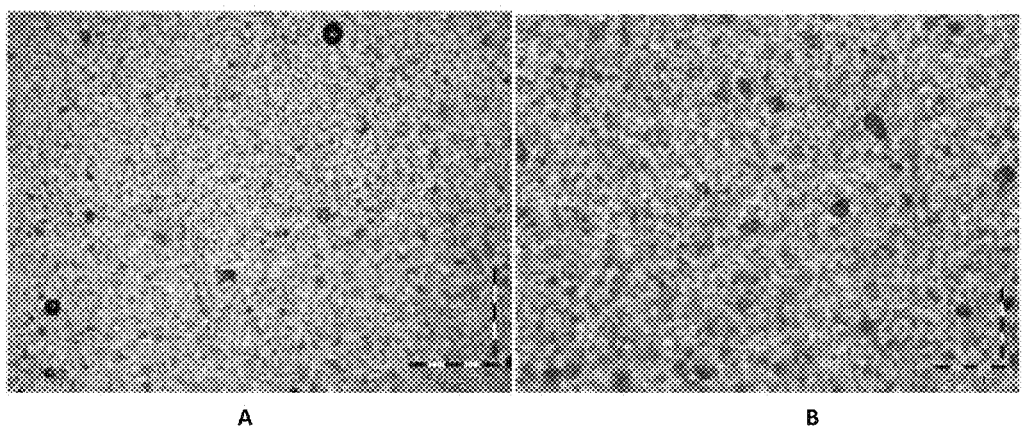
FIG. 12 illustrates an optical microscopic photograph showing biodegradable polymer, which is polylactic acid (PLA) introduced with a bio-based polymer additive prepared from yeast biomass at a ratio of 5.0% taken at 500× (Left)(A) and 1000× (Right)(B).

A Polymer Composition Comprising PLA and a Bio-based Polymer Additive Prepared from Yeast Biomass In this example, Poly Lactic Acid (PLA) 2002D from NatureWork was mixed with the bio-based polymer additive prepared from yeast biomass from Example 2 at ratio of about 0.5, 1.0, 3.0 and 5.0% by weight. The mixed material was then fed into an extruder, specifically an Extrusion Line and Mixer (Haake Rheometer Os), at feeding rate 1.5 g per minute, in which a screw was heated at temperature about 170° C. and the screw speed was set at 120 RPM. The extruded polymer composition was then cut with the Haake Rheometer OS to reduce the size. The mixture was then made into a dumbbell-shaped specimen using injector EC100II2A (Toshiba) with a capacity of 61 kg/h. Injection was done under an injection pressure of 200 MPa, at a Barrel temperature of 165° C. and a mold temperature of 40° C. Then, the finished specimen (FIG. 4) was subjected to performance test.

It was noted that in all examples 3-6, with the use of the composition comprising PBS or PLA and the bio-based polymer additive prepared from microalgae or yeast biomass of broken microorganism cell according to the present invention, both the PBS and PLA can be mixed efficiently with the additive without the addition of a compatibility agent, like an oil as a way to enhance mixing efficiency.

Further, it should be noted that it is possible to vary the ratio between the bio-based polymer additive and the biodegradable polymer depending on the required properties of the final product. According to the present invention and examples, different ratio of bio-based polymer additive and the biodegradable polymer were determined based on the maintaining mechanical properties of the biodegradable polymer composition. The range of the bio-based polymer additive is from 0.05-10% by weight, preferably 0.5-5% by weight. FIGS. 1 to 17 illustrate various characteristics and properties of molded article of biodegradable polymer composition produced using the bio-based polymer additive according to the present invention. It is also noted that when the weight % of the bio-based polymer additive is less than 0.05, the properties of the bio-based polymer additive is significantly reduced and hence the biodegradable polymer composition produced from the biodegradable polymer comprising the said additive does not possess the required properties. In contrast, undesirable mechanical properties have been observed in the biodegradable polymer composition comprising more than 10% by weight of bio-based polymer additive.

Accordingly, the biodegradable polymer composition produced with biodegradable polymer comprising bio-based polymer additive prepared from the biomass of broken microorganism cell according to the present invention demonstrates higher polymer properties, as an example, as well as enhance production efficiency. These advantages will be more apparent in view of the following comparative examples:

COMPARATIVE EXAMPLE 1

In the same manner as in Examples 3 and 5, the PBS composition was prepared without using of bio-based polymer additive prepared from microalgae or yeast biomass according to this invention. The composition was then extruded and molded into a molded article. Then the finished specimen was subjected to performance tests.

COMPARATIVE EXAMPLE 2

In the same manner as in Examples 4 and 6, the PLA composition was prepared without using of bio-based polymer additive prepared from microalgae or yeast biomass according to this invention. The composition was then extruded and molded into a molded article. Then the finished specimen was subjected to performance tests.

Determination of Mechanical Properties of Biodegradable Polymer Composition Comprising Bio-based Polymer Additive Derived from Microalgae or Yeast Biomass According to this Invention Mechanical properties of biodegradable polymers from Examples 3 to 6, and Comparative Example 1 and 2 were determined using the below described method. The results are as shown in Table 1. Tensile strength and elongation at break were tested in accordance with method specified by ASTM D638 using Universal testing Machine, Brand: Zwick/Roell, Model: Z050 TE. Tests were carried out at a temperature of 23° C. and humidity of 50%. Breaking tensile stress was determined by equation (1), while breaking elongations was determined by equation (2).

$$\text{Tensile strength}(MPa) = \text{breaking load}(N)/\text{cross section}(mm^2) \quad (1)$$

$$\text{Elongation at break}(\%) = [(\text{breaking elongation} - \text{span length})/\text{span length}] \times 100 \quad (2)$$

TABLE 1

Mechanical properties of biodegradable polymer composition containing bio-based polymer additive

| Sample Name | E (MPa) | Tensile Stress | | | Elongation at Break (%) |
| --- | --- | --- | --- | --- | --- |
| | | at Yield | at Max | at Break | |
| PLA without additive | 3740 ± 86 | 77.5 ± 0.5 | 77.5 ± 0.5 | 65.7 ± 1.2 | 5.1 ± 0.9 |
| PLA + microalgae 0.5% | 3800 ± 74 | 71.9 ± 0.7 | 71.9 ± 0.7 | 59.3 ± 1.8 | 5.4 ± 1.4 |
| PLA + microalgae 1% | 3750 ± 127 | 69.1 ± 0.4 | 68.5 ± 1.0 | 61.8 ± 5.4 | 3.5 ± 1.4 |
| PLA + microalgae 3% | 3650 ± 101 | 64.1 ± 0.9 | 64.1 ± 0.9 | 53.6 ± 0.9 | 4.6 ± 0.8 |
| PLA + microalgae 5% | 3760 ± 56 | 62.0 ± 0.2 | 57.4 ± 6.9 | 53.6 ± 4.9 | 2.4 ± 1.0 |

TABLE 1-continued

Mechanical properties of biodegradable polymer composition containing bio-based polymer additive

| Sample Name | E (MPa) | Tensile Stress | | | Elongation at Break (%) |
| --- | --- | --- | --- | --- | --- |
| | | at Yield | at Max | at Break | |
| PLA + Yeast 0.5% | 3830 ± 145 | 69.3 ± 0.3 | 69.3 ± 0.3 | 59.6 ± 3.2 | 5.7 ± 2.3 |
| PLA + Yeast 1% | 3920 ± 168 | 66.7 ± 0.3 | 66.7 ± 0.3 | 55.3 ± 1.3 | 5.9 ± 1.0 |
| PLA + Yeast 3% | 3720 ± 127 | 59.2 ± 0.6 | 59.2 ± 0.6 | 51.4 ± 4.4 | 5.9 ± 3.1 |
| PLA + Yeast 5% | 3790 ± 90 | 56.4 ± 0.3 | 56.4 ± 0.3 | 50.2 ± 3.2 | 3.2 ± 0.8 |
| PBS without additive | 786 ± 26 | 41.4 ± 0.3 | 41.4 ± 0.3 | 40.4 ± 0.9 | 17 ± 1.7 |
| PBS + microalgae 0.5% | 815 ± 31 | 41.1 ± 0.4 | 40.9 ± 0.5 | 40.3 ± 1.0 | 16 ± 2.3 |
| PBS + microalgae 1% | 814 ± 8.5 | 40.0 ± 0.2 | 40.1 ± 0.2 | 38.6 ± 1.6 | 16 ± 1.1 |
| PBS + microalgae 3% | 829 ± 15 | 36.7 ± 0.2 | 36.8 ± 0.2 | 35.9 ± 0.9 | 13 ± 1.2 |
| PBS + microalgae 5% | 862 ± 28 | 34.7 ± 0.4 | 34.6 ± 0.3 | 34.0 ± 0.4 | 12 ± 0.8 |
| PBS + Yeast 0.5% | 799 ± 23 | 40.5 ± 0.5 | 40.5 ± 0.3 | 39.8 ± 0.8 | 16 ± 1.5 |
| PBS + Yeast 1% | 814 ± 34 | 39.3 ± 0.1 | 39.2 ± 0.2 | 38.5 ± 0.9 | 14 ± 0.8 |
| PBS + Yeast 3% | 828 ± 47 | 37.0 ± 0.2 | 37.0 ± 0.3 | 36.3 ± 0.6 | 14 ± 0.7 |
| PBS + Yeast 5% | 869 ± 38 | 34.8 ± 0.2 | 35.1 ± 0.4 | 34.4 ± 0.9 | 14 ± 1.0 |

The result showed that the mechanical properties of both PLA and PBS resin containing the bio-based polymer additive were reduced according to the increase of additive contents. This suggested that the undesired mechanical properties would be a limitation of percentage of additive incorporated in PLA and PBS resin.

Determination of Thermal Properties of Biodegradable Composition Containing Bio-based Polymer Additive According to this Invention Thermal properties of the biodegradable polymer compositions comprising bio-based polymer additive pigments were assayed by using Differential Scanning calorimeter (DSC), Brand: NETZSCH, Model: DSC 204 F1 in accordance with method specified by ASTM D3418. Furthermore, the blended resins were also assayed by using Thermal Gravimetric Analyser (TGA), Brand: NETZSCH, Model: TG 209 F1. The results were shown in Table 2.

TABLE 2

Thermal properties of biodegradable plastic, PBS and PLA containing with bio-based polymer additive according to this invention

| Sample name | Tm (deg C.) | Tg/Tc (deg C.) | Td (deg C.) |
| --- | --- | --- | --- |
| PLA 2002D | 152.9 | 57.1 | 358 |
| PLA 0.5% Algae | 156.1 | 56.2 | 348 |
| PLA 1% Algae | 155.4 | 54.9 | 328 |
| PLA 3% Algae | 152.9 | 52.1 | 320 |
| PLA 5% Algae | 148.5 | 48.4 | 302 |
| PLA 0.5% Yeast | 155.0 | 56.4 | 349 |
| PLA 1% Yeast | 155.3 | 55.8 | 356 |
| PLA 3% Yeast | 155.1 | 53.7 | 341 |
| PLA 5% Yeast | 154.8 | 53 | 337 |
| PBS FZ71PD | 113.6 | 68.5 | 378 |
| PBS 0.5% Algae | 113.8 | 70.8 | 382 |
| PBS 1% Algae | 113.7 | 71.0 | 377 |
| PBS 3% Algae | 113.5 | 69.7 | 376 |
| PBS 5% Algae | 113.3 | 69.3 | 373 |
| PBS 0.5% Yeast | 113.7 | 69.5 | 384 |
| PBS 1% Yeast | 113.6 | 70.9 | 384 |
| PBS 3% Yeast | 113.3 | 70.8 | 383 |
| PBS 5% Yeast | 113.1 | 70.3 | 381 |

Figure 13:
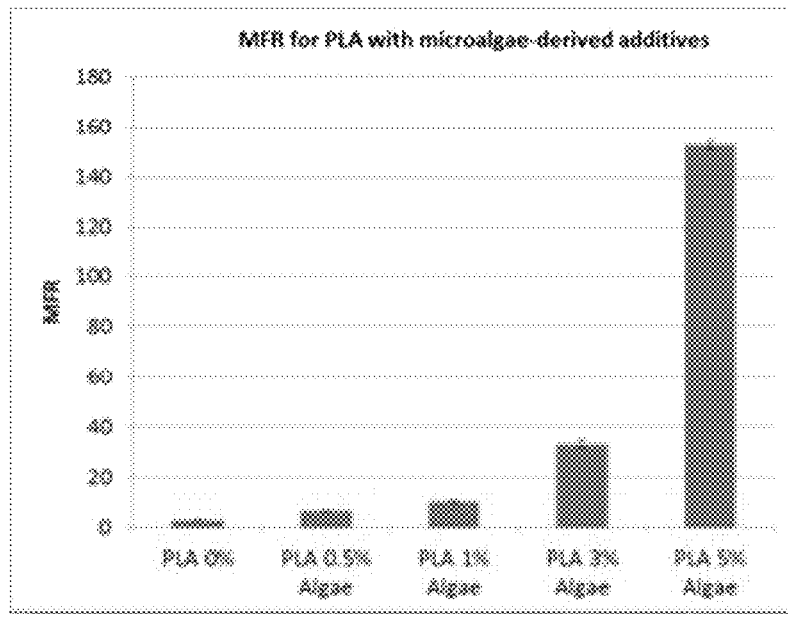
FIG. 13 illustrates a bar chart showing the Melt Flow Rate (MFR) values of polylactic acid (PLA) polymers introduced with microalgae-derived additives according to exemplary embodiments of the present invention.
Figure 14:
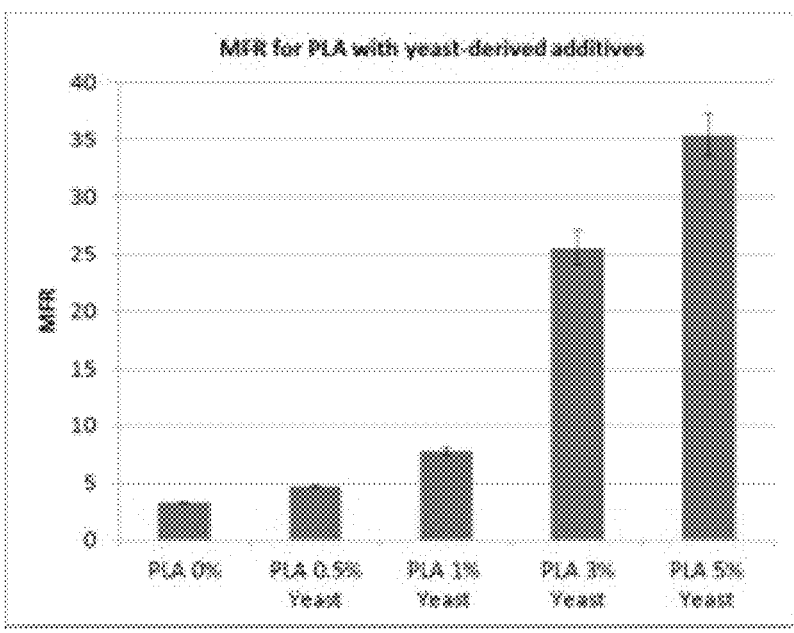
FIG. 14 illustrates a bar chart showing the Melt Flow Rate (MFR) values of polylactic acid (PLA) polymers introduced with yeast-derived additives according to exemplary embodiments of the present invention.

Tm = Melting Temperature;
Tg = Glass Transition Temperature;
Tc = Temperature at crystallization point;
Td = Decomposition Temperature Rheological Test of Biodegradable Polymer Composition Comprising the Bio-based Polymer Additive According to this Invention Rheological property at low shear rate was determined by Melt Flow Rate (MFR). MFR was determined by using Melt Flow indexer, Brand: Gottfert, Model: MI-4 at testing conditions=PLA: 2.16 kg, 190° C. As shown in FIG. 13, MFR values of PLA polymer compositions with microalgae biomass were drastically increased according to the amount of additional particles. Moreover, MFR value of PLA polymer composition with yeast biomass also increased according to the amount of additional particles as shown in FIG. 14. The addition of microalgae and yeast biomass cause an increase of rheological properties i.e., lowering viscosity of PLA polymer. The lowered viscosity is an advantage during formation into products.

Biodegradability Test of Biodegradable Polymer Composition Produced from Biodegradable Polymer Comprising the Bio-based Polymer Additive According to this Invention The term biodegradable polymer composition normally refers to an attack by microorganisms on nonwater-soluble polymer-based materials (plastics). This implies that the biodegradation of polymer is usually a heterogeneous process. Because of a lack of water-solubility and the size of the polymer molecules, microorganisms are unable to transport the polymeric material directly into the cells where most biochemical processes take place; rather, they must first excrete extracellular enzymes which depolymerize the polymers outside the cells. As a consequence, if the molar mass of the polymers can be sufficiently reduced to generate water-soluble intermediates, these can be transported into the microorganisms and fed into the appropriate metabolic pathway(s). As a result, the end-products of these metabolic processes include water, carbon dioxide and methane (in the case of anaerobic degradation), together with a new biomass.

By using Static-Incubation Titrimeric Determination (Zibilske et al., 1994. Carbon mineralization. Chapter 38. P. 835-863. *In Methods of Soil Analysis*, Part 2. Microbiological and Biochemical Properties. SSSA Book Series No. 5 Soil Science Society of America, Madison Wis.), the determination the $CO_2$ evolution of polymers was conducted. The PBS polymers containing bio-based polymer additive from Example 3 and 5, and Comparative Example 1 was prepared into powder using Grinder Ultra Centrifuge (Retsch). Each sample was mixed with fertilizer with 1 part sample and 99 parts fertilizer by weight. The tests were conducted in normal temperature (37±2° C.). Humidity was kept at 60±5% during the test. The testing period was 3 months long. Blank test was conducted by using domestic soil. Increase of biodegradability was determined by equation (3).

Increase of biodegradability (%)=[(CO$_2$ evolution of polymer composition containing bio-based additive)−CO$_2$ evolution of polymer composition without bio-based additive)/CO$_2$ evolution of polymer composition without bio-based additive]×100    (3)

Figure 15:
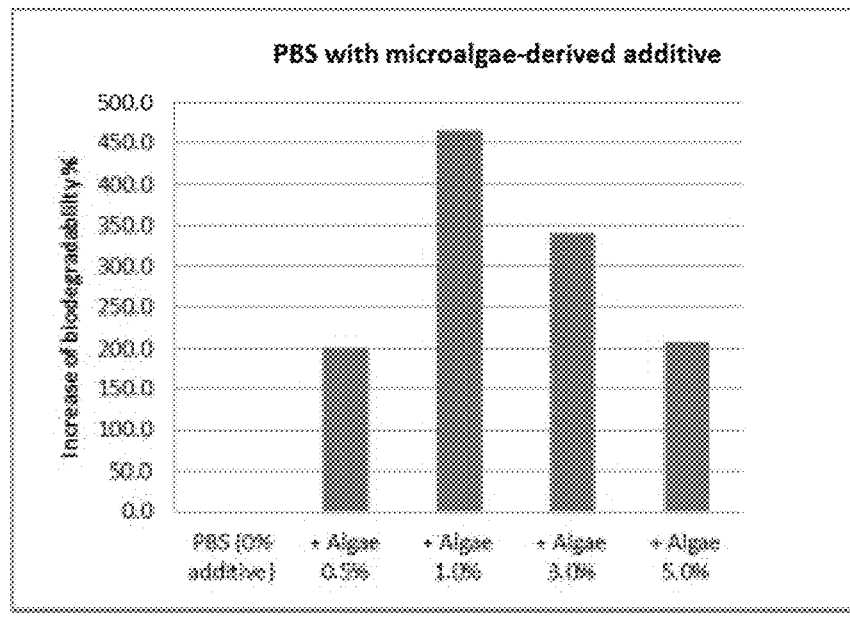
FIG. 15 illustrates a bar chart showing the percentage of increased of biodegradability of poly(butylene succinate) (PBS) polymers introduced with microalgae-derived additives according to exemplary embodiments of the present invention.
Figure 16:
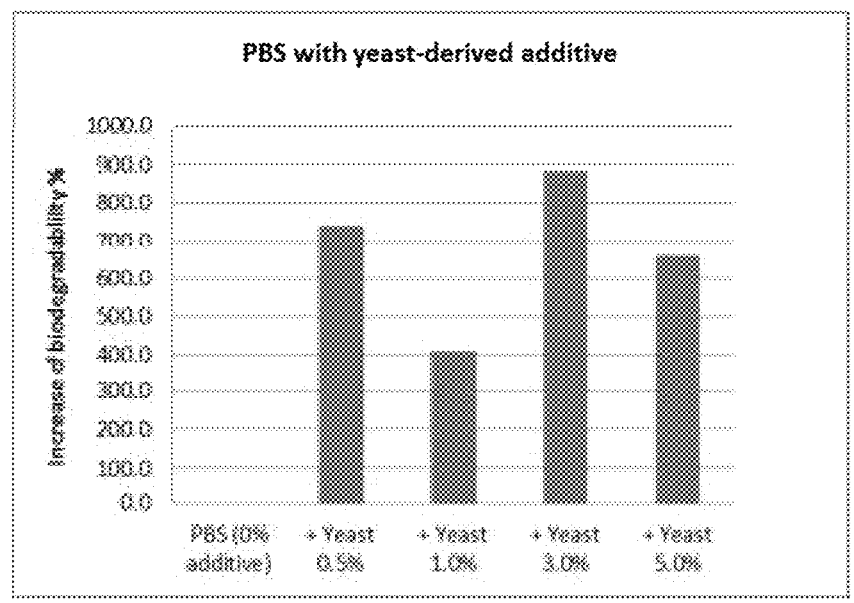
FIG. 16 illustrates a bar chart showing the percentage of biodegradability of poly(butylene succinate) (PBS) polymers introduced with yeast-derived additives according to exemplary embodiments of the present invention.
Figure 17:
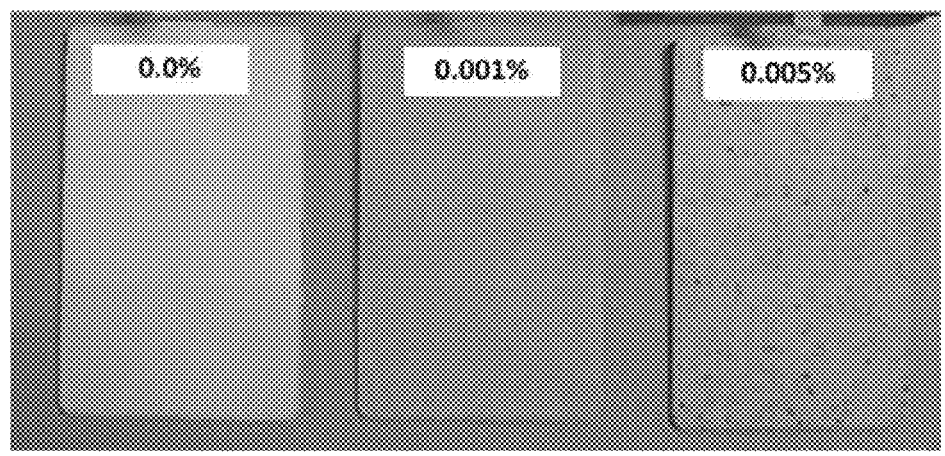
FIG. 17A illustrates a photograph showing biodegradable polymer, which is poly(butylene succinate) (PBS) introduced with 0%, 0.001% and 0.005% by weight of *Spirulina* cells without the breaking of cells according to the prior application.
FIG. 17B illustrates a photograph showing biodegradable polymer, which is poly(butylene succinate) (PBS) introduced with 0%, 0.5%, 1.0%, 3.0% and 5.0% by weight of *Spirulina* cells which are broken as described in the present invention.
Figure 17:
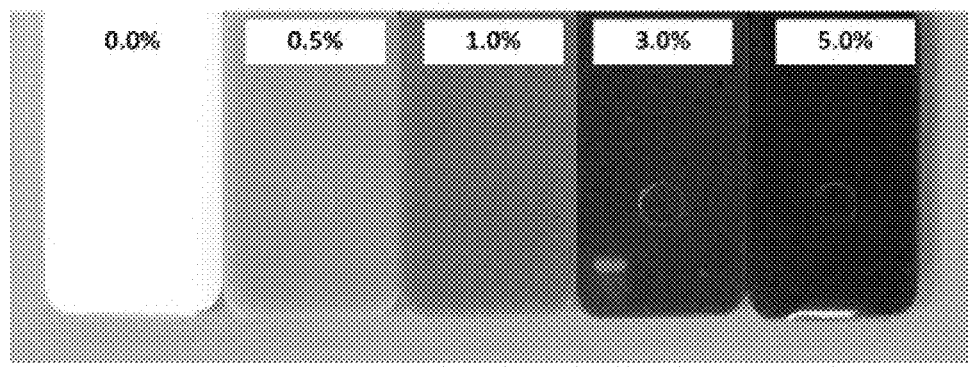

Results are shown in FIG. 15 and FIG. 16 where the biodegradable polymer compositions with the bio-based additive prepared from microalgae and yeast biomass according to this invention show increase in biodegradability compared to polymer with no additive.

Determination of Color Properties of Biodegradable Polymer Composition Containing Bio-based Polymer Additive According to this Invention Color appearance found in the biodegradable polymer comprising bio-based polymer additive pigment were assayed in accordance with method specified by ASTM E313 using Color Spectrophotometer, Brand: Data Color, Model: D 650. The results were shown in Table 3.

TABLE 3

Colors of biodegradable plastic, PBS and PLA containing bio-based polymer additive according to this invention

| Sample name | DE | DL | Da | Db |
|---|---|---|---|---|
| PLA 2002D | 0.11 | −0.11 | 0.01 | 0.02 |
| PLA + 1% Algae pigment powder | 45.77 | −45.65 | 3.28 | 0.35 |
| PLA + 5% Algae pigment powder | 50.97 | −50.34 | 2.87 | −7.41 |
| PLA + 1% Yeast pigment powder | 35.40 | −27.27 | 8.77 | 20.80 |
| PLA + 5% Yeast pigment powder | 42.87 | −41.57 | 10.08 | 2.88 |
| PBS FZ71PD | 0.13 | −0.13 | 0.00 | 0.01 |
| PBS + 1% Algae pigment powder | 39.19 | −35.05 | −7.64 | 15.81 |
| PBS + 5% Algae pigment powder | 50.00 | −49.28 | −1.62 | 8.30 |
| PBS + 1% Yeast pigment powder | 22.53 | −13.03 | 4.49 | 17.83 |
| PBS + 5% Yeast pigment powder | 38.22 | −27.75 | 10.58 | 24.06 |

DL = Differentiated lightness of each sample against the standard samples, PLA 2002D or PBS FZ71PD; while 100 for perfect white to zero for black
Da = Differentiated redness and greenness of each sample against the standard samples, PLA 2002D or PBS FZ71PD; while redness when positive, gray when zero, and greenness when negative
Db = Differentiated yellowness and blueness of each sample against the standard samples, PLA 2002D or PBS FZ71PD; while yellowness when positive, gray when zero, and blueness when negative
DE = (DL$^2$ + Da$^2$ + Db$^2$)$^{1/2}$ Particle Distribution Distribution of particles of algae additive pigment powder and yeast additive pigment powder in PBS were observed under a Cannon microscope. The results are shown in FIGS. 5, 6, 9 and 10. Distribution of particles of algae additive pigment powder and yeast additive pigment powder in PLA were observed under a Cannon microscope. The results are shown in FIGS. 7, 8, 11 and 12.

The biodegradable polymer composition according to the invention shows good compatibility with conventional biodegradable polymers such as PLA and PBS without further addition of compatibility agent, like an oil. They do not cause serious effects to mechanical properties of each polymer, thus satisfying the use as polymer additives in several aspects.

It is important to note that compared to unbroken microorganism cells, broken microorganism cells of the biomass provide more compatibility of biodegradable polymer and bio-based additive, and therefore enhance the properties and characteristics, including color properties, of biodegradable polymer composition produced therefrom. This can be seen in FIG. 17, which shows large agglomeration of unbroken *Spirulina* cell added in the PBS polymer at very low content (0.005% of unbroken cell). On the other hand, the FIG. 18 clearly illustrates very well compatibility of the additive prepared from broken cell of *Spirulina* microalgae biomass according to the present invention in the PBS polymer at high content (5% or 1,000 times higher than the addition of unbroken cell). Therefore, the present invention suggested that the step of breaking microorganism cell is important to prepare the microorganism-derived bio-based polymer additives without further additives.

Furthermore, the bio-based polymer additives according to the present invention are completely degradable because they are bio-based materials. Therefore, the degradation of the biodegradable polymer composition does not leave toxic substances in the soil. It is safe for use as food packaging products or other applications relating to animal and human use.

Since adding the bio-based polymer additives lowers the viscosity of biodegradable polymer composition, failed injection for biodegradable polymer composition injection grade is lowered. At the same time extrusion of this biodegradable polymer composition is better over ordinary biodegradable polymer composition due to lowered viscosity. The bio-based polymer additive also accelerates biodegradability of PLA and PBS.

From the above, it is shown that bio-base additive pigments such as those derived from biomass of microorganisms including microalgae, yeast, and bacteria work well with PBS and PLA plastics. Further, it is also shown that both PBS and PLA can be colored well using bio-base additive pigment powder from microorganism biomass without the addition of oil to enhance mixing efficiency. The derived bio-degradable plastic at different percentage of additive pigments powders demonstrates various properties suited for various applications of the plastic in various industries.

Finally, it is clear from the description and data according to the present invention that is possible to provide biodegradable plastic of which bio-base additive, for example bio-based additive pigment, in particular from microorganism biomass such as of microalgae, yeast, bacteria. The biodegradable plastic according to the present invention offer better solution to reduce environmental problems, the production is viable, sustainable and economical.

The invention claimed is:

1. A bio-based polymer additive, for use in manufacturing of biodegradable polymer, wherein the additive is the entire biomass of broken microorganism cells in a powder or concentrated form, and the microorganism is selected from the group consisting of Division of Cyanophyta, Prochlorophyta, Dinophyta, Chrysophyta, Prymnesiophyta, Bacillariophyta, Xanthophyta, Eustigmatophyta, Rhaphidophyta, Phaeophyta, Proteobacteria, Cyanobacteria, Eubacteria, Spirochetes, Chlamydiae, Zygomycota, Eumycota, and combinations thereof.

2. The bio-based polymer additive according to claim 1, wherein the entire biomass of broken microorganism cells comprises at least one color molecule.

3. The bio-based polymer additive according to claim 2, wherein the color molecule is selected from the group consisting of anthocyanins, chlorophylls, carotenoids, phycobilins, and mixtures thereof.

4. The bio-based polymer additive according to claim 1, wherein the microorganism from Division of Cyanophyta is *Spirulina*.

5. The bio-based polymer additive according to claim 1, wherein the microorganism from Division of Eumycota is *Saccharomyces*.

6. The bio-based polymer additive according to claim 1, wherein the additive is in powder form.

7. A biodegradable polymer composition, comprising:
   at least one bio-based polymer additive according to claim 1, which is present in an amount ranging from 0.05 to 10% by weight; and
   a biodegradable polymer.

8. The biodegradable polymer composition according to claim 7, wherein the bio-based polymer additive ranges from 0.5 to 5% by weight.

9. The biodegradable polymer composition according to claim 7, wherein the at least one bio-based polymer additive comprises at least one color molecule.

10. The biodegradable polymer composition according to claim 9, wherein the color molecule is selected from the group consisting of anthocyanins, chlorophylls, carotenoids, phycobilins, and mixtures thereof.

11. The biodegradable polymer composition according to claim 7, wherein the at least one bio-based polymer additive is the entire biomass of broken *Spirulina* cells in a powder or concentrated form.

12. The biodegradable polymer composition according to claim 7, wherein the at least one bio-based polymer additive is the entire biomass of broken *Saccharomyces* cells in a powder or concentrated form.

13. The biodegradable polymer composition according to claim 7, wherein the biodegradable polymer is selected from biodegradable polyesters.

14. The biodegradable polymer composition according to claim 7, wherein the biodegradable polymer is poly(butylene succinate) (PBS) or polylactic acid (PLA) or a mixture thereof.

15. The biodegradable polymer composition according to claim 7, wherein the bio-based polymer additive increases the melt flow rate of the polymer compared to the same polymer in the absence of the bio-based polymer additive.

16. The biodegradable polymer composition according to claim 7, wherein the bio-based polymer additive enhances the biodegradability property of the polymer, as compared to the same polymer in the absence of the bio-based polymer additive.

17. The biodegradable polymer composition according to claim 9, wherein the additive is for use as a pigment for coloring the biodegradable polymer composition.

18. A process for preparing a bio-based polymer additive from the biomass of broken microorganism cell comprising the steps of:
   a) providing microorganism biomass;
   b) mechanical breaking microorganism cell of the biomass of a) at a temperature of 20 to 80° C., wherein the mechanical cell breaking method is selected from the group consisting of a homogenization method using a rotational velocity of 10,000 rpm, a sonication method, a freeze-thaw method, a mortar and pestle method, and an ultrasonic method; and
   c) powdering or concentrating the entire biomass of broken microorganism cell obtained from step b).

19. The process according to claim 18, wherein the microorganism biomass is selected from the group consisting of Division of Cyanophyta, Prochlorophyta, Dinophyta, Chrysophyta, Prymnesiophyta, Bacillariophyta, Xanthophyta, Eustigmatophyta, Rhaphidophyta, Phaeophyta, Proteobacteria, Cyanobacteria, Eubacteria, Spirochetes, Chlamydiae, Zygomycota, Eumycota, and combinations thereof.

20. The process according to claim 18, wherein the microorganism comprises at least one color molecule.

21. The process according to claim 20, wherein the color molecule is selected from the group consisting of anthocyanins, chlorophylls, carotenoids, phycobilins, and mixtures thereof.

22. The process according to claim 18, wherein the microorganism biomass of step a) is collected from natural resources, bioreactors or fermenters, and added in aqueous solution at solid concentration of 50 to 200 gram per liter.

23. The process according to claim 18, wherein the step c) is a hot powdering method or cold powdering method.

24. The process according to claim 23, wherein the hot powdering method is selected from the group consisting of spray drying, evaporation, rotary drying, flash drying, disk drying, cascade drying, and superheated steam drying.

25. The process according to claim 23, wherein the cold powdering method is selected from the group consisting of freeze drying, spray congealing, and spray cooling.

26. A method for coloring a biodegradable polymer, comprising adding a bio-based polymer additive according to claim 2 to a biodegradable polymer.

27. A method of increasing the melt flow rate of a biodegradable polymer, comprising adding a bio-based polymer additive according to claim 1 to a biodegradable polymer, wherein the melt flow rate of the biodegradable polymer is increased in comparison to the melt flow rate of the same polymer in the absence of the bio-based polymer additive.

28. A method of enhancing the biodegradability property of a biodegradable polymer, comprising adding a bio-based polymer additive according to claim 1 to a biodegradable polymer, wherein the biodegradability of the biodegradable polymer is enhanced in comparison to the biodegradability of the same polymer in the absence of the bio-based polymer additive.

29. An article of manufacture prepared with the biodegradable polymer composition according to claim 7.

30. A process for preparing a bio-based polymer additive from the biomass of broken microorganism cell consisting of the steps of:
   a) providing microorganism biomass;
   b) mechanical breaking microorganism cell of the biomass of a) at a temperature of 20 to 80° C., wherein the mechanical cell breaking method is selected from the group consisting of a homogenization method, a sonication method, a freeze-thaw method, a mortar and pestle method, and an ultrasonic method; and
   c) powdering or concentrating the entire biomass of broken microorganism cell obtained from step b).

* * * * *